US00PP19360P2

(12) United States Plant Patent
Kaagman

(10) Patent No.: US PP19,360 P2
(45) Date of Patent: Oct. 21, 2008

(54) *DAHLIA* PLANT NAMED 'GOALIA ORAN'

(50) Latin Name: *Dahlia variabilis*
Varietal Denomination: Goalia Oran

(75) Inventor: Pim Kaagman, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/894,580

(22) Filed: Aug. 21, 2007

(51) Int. Cl.
*A01H 5/00* (2006.01)

(52) U.S. Cl. ..... Plt./321

(58) Field of Classification Search ..... Plt./321
See application file for complete search history.

(56) References Cited

PUBLICATIONS

UPOV ROM GTITM Computer Database, GTI Jouve Retrieval Software 2007/05 Citations for 'Goalia Oran'.*

* cited by examiner

*Primary Examiner*—Wendy C. Haas
(74) *Attorney, Agent, or Firm*—Jondle & Associates, P.C.

(57) ABSTRACT

A new *Dahlia* plant particularly distinguished by its large, orange-red flowers, a full plant habit, and large, nearly entire dark leaves is disclosed.

2 Drawing Sheets

Genus and species: *Dahlia variabilis.*
Variety denomination: 'Goalia Oran'.

BACKGROUND OF THE NEW PLANT

The present invention comprises a new and distinct cultivar of *Dahlia,* botanically known as *Dahlia variabilis,* and hereinafter referred to by the cultivar name 'Goalia Oran'. The new cultivar originated from a hybridization made in June 1999 in Andijk, The Netherlands. The female parent was the bronze-yellow-flowered *Dahlia* proprietary line 'DT-32-3' (unpatented), and the male parent was the orange-flowered *Dahlia* proprietary line 'DU-43-1' (unpatented). The seeds produced by the hybridization were sown in February 2002 in Andijk, The Netherlands. A single plant selection was chosen for further evaluation and for asexual propagation in May 2002 in Andijk, The Netherlands.

The new cultivar was created in 1999 in Andijk, The Netherlands and has been asexually reproduced repeatedly by vegetative cuttings and tissue culture in Andijk, The Netherlands, and Gilroy, Calif. over a five-year period. The plant has also been trialed at Gilroy, Calif, Michigan, Andijk, The Netherlands and Hillscheid, Germany. The present invention has been found to retain its distinctive characteristics through successive asexual propagations.

Plant Breeder's Rights for this cultivar were applied for in the European Union on Jun. 19, 2006 and in Canada on Oct. 3, 2006. 'Goalia Oran' has not been made publicly available more than one year prior to filing of this application.

SUMMARY OF THE INVENTION

The following are the most outstanding and distinguishing characteristics of this new cultivar when grown under normal horticultural practices in Gilroy, Calif.

1. Large, orange flowers;
2. A full plant habit; and
3. Small, dark green leaves.

DESCRIPTION OF THE PHOTOGRAPHS

This new *Dahlia* plant is illustrated by the accompanying photographs which show overall plant habit including blooms, buds, and foliage of the plant; the photographs are of 20-to 24-week old plants grown in a greenhouse in Hillscheid, Germany in 2006; the colors shown are as true as can be reasonably obtained by conventional photographic procedures.

DESCRIPTION OF THE NEW CULTIVAR

Figure 1:
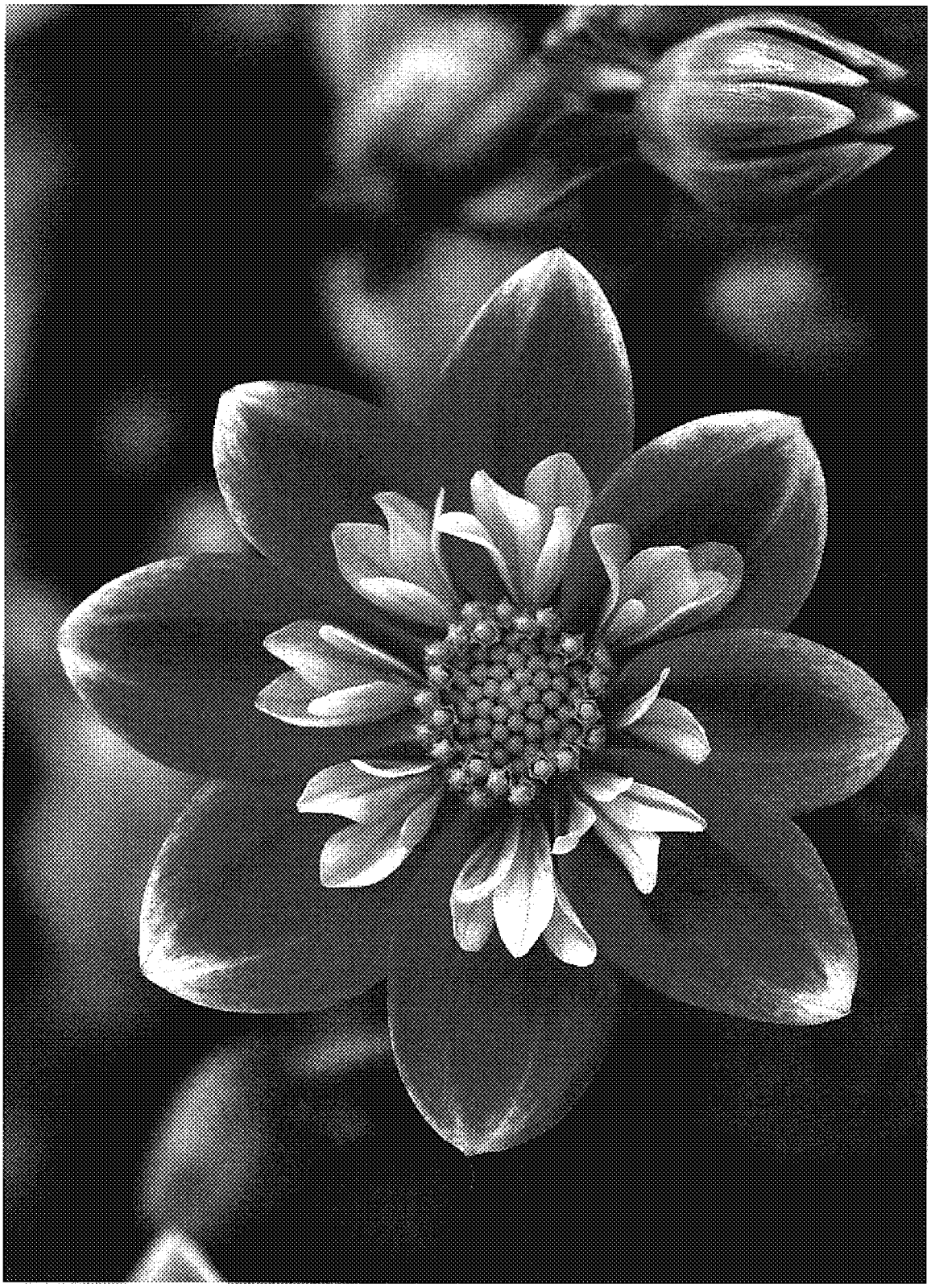
FIG. 1 shows a close-up of the mature flowers.
Figure 2:
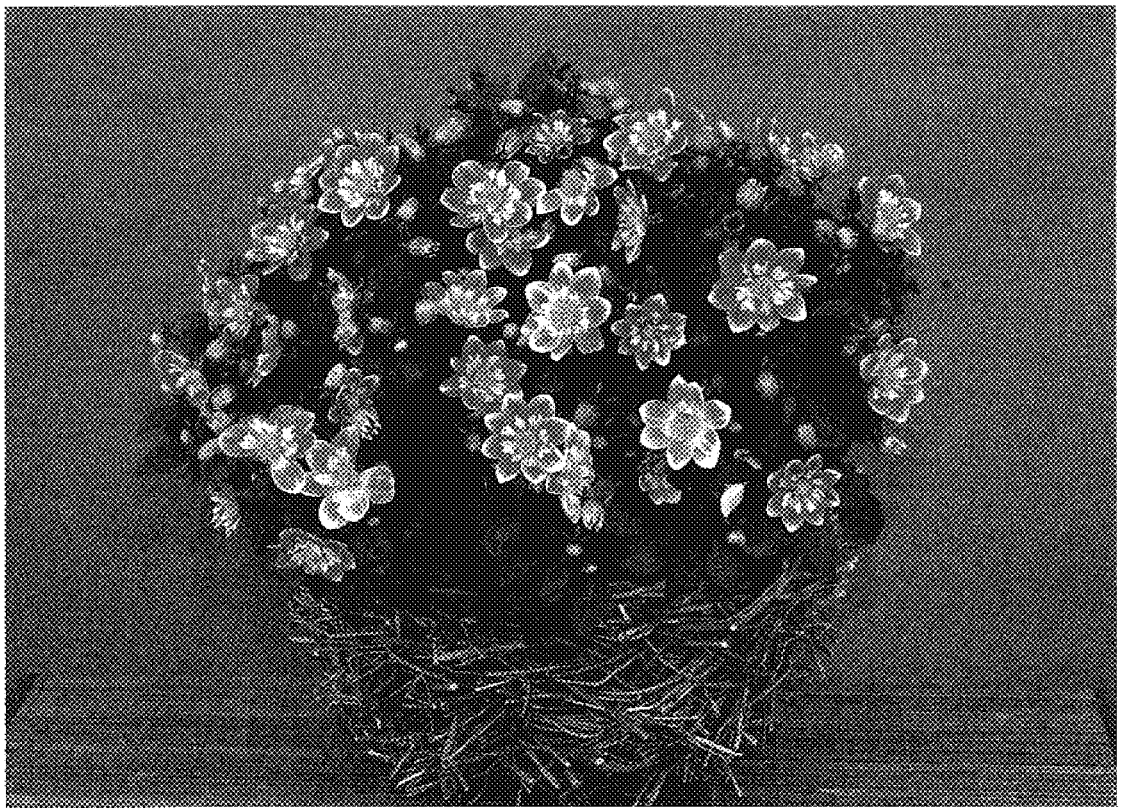
FIG. 2 shows the overall plant habit, including blooms, buds, and foliage.

The following detailed descriptions set forth the distinctive characteristics of 'Goalia Oran'. The data which define these characteristics were collected from asexual reproductions carried out in Ontario, Canada. The plant history was taken on 16-week-old plants grown in 6-inch azalea pots in the spring and summer seasons in a greenhouse. Two terminal pinches were made at a young plant stage. No plant growth regulators were used. The plants were grown under a poly covered hoop and then moved indoors. Color readings were taken outdoors in the summer season under natural light. Color references are primarily to the R.H.S. Colour Chart of The Royal Horticultural Society of London (R.H.S.) (2001 edition).

DESCRIPTION OF THE NEW PLANT

Classification:
*Family.*—Asteraceae.
*Botanical name.*—*Dahlia variabilis.*

Parentage:
*Female parent.*—'DT-32-3' bronze-yellow-flowered *Dahlia* proprietary line (unpatented).
*Male parent.*—'DU-43-1' orange-flowered *Dahlia* proprietary line (unpatented).

Growth:

*Form.*—Upright.

*Habit.*—Compact and mounding.

*Growth and branching habit.*—Good, vigorous habit; excellent branching.

*Height* (*from top of soil*).—19.0 cm to 21.0 cm.

*Width.*—31.0 cm to 34.0 cm.

*Time to produce a finished flowering plant.*—9 to 12 weeks for a 4-to 6-inch pot.

*Outdoor plant performance.*—Free flowering, used in patio planters, mixed-container plantings, or in garden beds.

*Time to initiate and develop roots.*—21 to 28 days.

*Root description.*—Fibrous and white.

Leaves:

*Arrangement.*—Opposite, single, simple.

*Shape.*—Elliptical.

*Apex.*—Obtuse to acute.

*Base.*—Attenuate.

*Margin.*—Almost entire, but with a few serrations.

*Length* (*fully expanded*).—7.5 cm to 7.7 cm.

*Width* (*fully expanded*).—3.0 cm to 3.2 cm.

*Texture.*—Leathery, smooth.

*Color.*—Immature: Upper surface: RHS 137B. Lower surface: RHS 148D with a silvery sheen. Mature: Upper surface: RHS 137A. Lower surface: RHS 148D with a silvery sheen.

*Venation.*—Arrangement: Pinnate. Color: RHS 143C.

*Petiole.*—Color: Transparent green with RHS 143C along the sides. Length: 1.9 cm to 2.1 cm. Width: 0.4 cm. Texture: Smooth, glabrous.

Stems:

*Number of branches per plant.*—4 to 6.

*Length.*—17.0 cm to 19.0 cm.

*Diameter.*—0.4 cm.

*Internode length.*—1.8 cm to 2.0 cm.

*Color.*—RHS 146B, with some RHS 143C blotches mixed in.

*Texture.*—Smooth, glabrous.

*Anthocyanin.*—Absent.

*Penduncle.*—Color: Closest to RHS 144C. Length: 7.5 cm to 7.8 cm. Diameter: 0.2 cm. Texture: Smooth, glabrous.

Bud:

*Shape.*—Orbicular when immature, to ovate when mature.

*Diameter.*—0.8 cm to 1.0 cm.

*Length.*—0.7 cm to 0.9 cm.

*Color* (*just before ray florets unfold*).—RHS 30A with some RHS 1C at the apex.

Inflorescence:

*Type.*—Composite; borne on terminals above foliage; semi-double flowers, florets face upward or outward.

*Blooming habit.*—Continuous throughout the growing season; excellent floriferousness.

*Quantity of inflorescences per plant.*—15 to 20.

*Lastingness of individual blooms on the plant.*—7 to 12 days.

*Fragrance.*—None.

*Inflorescence diameter.*—5.1 cm to 5.6 cm.

Disc floret:

*Quantity* (*per inflorescence*).—50 to 60.

*Shape.*—Elongated, cylindrical, shiny.

*Color.*—Closest to RHS 17A.

*Length.*—1.0 cm to 1.1 cm.

*Diameter.*—0.2 cm to 0.3 cm.

*Apex.*—5-pointed, each acute.

*Ray floret.*—Length: 2.6 cm to 2.8 cm. Width: 1.7 cm to 1.9 cm. Color: Immature: Upper surface: RHS 43A with varying size blotches of RHS 2B at the apex. Lower surface: RHS 28A with a few blotches of RHS N34B and longitudinal stripes of RHS 1C. Mature: Upper surface: Between RHS N30A and RHS N30B basally and becoming irregularly mottled with RHS 1C towards the margins and mostly has a solid apex of RHS 1C; Maturing to between RHS 30A, RHS 30B and RHS 30C with a larger mottled area of RHS 1C and RHS 1D and a larger solid margin at the apex of RHS 1D. Lower surface: RHS 28A with a few blotches of RHS N34B and longitudinal stripes of RHS 1C.

*Apex.*—Mucronate. Base: Fused. Margin: Entire. Texture: Papillose.

*Petaloids.*—Quantity: 3 to 4 per ray floret. Color (both surfaces): Closest to and between RHS 1A and RHS 1C, some with a small blotch of RHS N30B. Length: 1.5 cm to 1.7 cm. Diameter: 0.5 cm. Shape: Narrow elliptic. Apex: Acute. Margin: Entire. Base: Attenuate. Texture: Papillose.

*Involucral bracts.*—Quantity (per inflorescence): 5. Shape: Elliptical, almost spatulate. Length: 0.9 cm to 1.0 cm. Width: 0.4 cm to 0.5 cm. Color (both surfaces): RHS 137B. Apex: Acute. Base: Fused. Margin: Entire. Texture: Smooth, glabrous.

Reproductive organs:

*Androecium.*—Location: Present on disc florets only. Quantity per floret: 1. Anther: Color: RHS 13A. Length: 0.4 cm. Filament length: 0.9 cm. Filament color: RHS N155C. Pollen color: RHS 13A. Pollen amount: Moderate.

*Gynoecium.*—Location: Present on ray and disc florets. Quantity per floret: 1. Pistil length: Ray florets: 0.9 cm. Disc florets: 1.3 cm. Stigma: Color: RHS 3A. Style: Color: Between RHS 154B and RHS 154C.

Fruit and seed set: Has not been observed.

Disease and insect resistance: Has not been observed.

COMPARISON WITH PARENTAL AND COMMERCIAL CULTIVARS

'Goalia Oran' differs from the female parent, 'DT-32-3' (unpatented) in that 'Goalia Oran' has larger, orange-red flowers with darker green leaves, while 'DT-32-3' has bronze-yellow flowers with lighter green leaves.

'Goalia Oran' differs from the male parent, 'DU-43-1' (unpatented) in that 'Goalia Oran' has larger, orange-red flowers with a large, fuller plant habit and better branching, while 'DU-43-1' has orange flowers and a smaller plant habit.

'Goalia Oran' differs from the commercial cultivar 'Barbados' (unpatented) (European Union Plant Variety Propection Application No. EU13541) in that 'Goalia Oran' is a collerette type, red-orange flower, with larger, nearly entire leaves, while 'Barbados' is a yellow decorative type flower with smaller, lobbed leaves.

I claim:

1. A new and distinct cultivar of *Dahlia* plant as shown and described herein.

* * * * *